United States Patent [19]

Bacskai

[11] 4,057,589

[45] Nov. 8, 1977

[54] HYDROXYLATION OF UNSATURATED DIOLS TO PREPARE NOVEL TETRAOLS

[75] Inventor: Robert Bacskai, Kensington, Calif.

[73] Assignee: Chevron Research Company, San Francisco, Calif.

[21] Appl. No.: 697,594

[22] Filed: June 18, 1976

Related U.S. Application Data

[62] Division of Ser. No. 612,417, Sept. 11, 1975, Pat. No. 3,991,126.

[51] Int. Cl.$^2$ .................. C07C 29/02; C07C 29/10
[52] U.S. Cl. ................................................ 260/635 E
[58] Field of Search .................................. 260/635 E

[56] References Cited

U.S. PATENT DOCUMENTS

| | | | |
|---|---|---|---|
| 2,623,909 | 12/1952 | Robeson et al. | 260/635 E |
| 3,053,856 | 9/1962 | Payne et al. | 260/635 E |
| 3,297,724 | 1/1967 | McConnell et al. | 260/635 E |
| 3,475,499 | 10/1969 | Winnick | 260/635 E |

Primary Examiner—Joseph E. Evans
Attorney, Agent, or Firm—D. A. Newell; John Stoner, Jr.; W. Keith Turner

[57] ABSTRACT

Tetraols of the formula

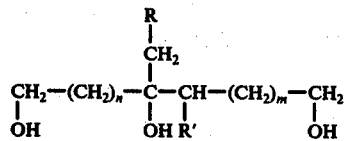

wherein R is hydrogen or hydroxy; R' is hydrogen or hydroxy and differs from R; $n$ is an integer from 1 to about 6; and $m$ is an integer from 0 to 6, are prepared by epoxidation of select unsaturated diols to form 1,2-epoxides, followed by hydroxylation of the epoxides.

3 Claims, No Drawings

HYDROXYLATION OF UNSATURATED DIOLS TO PREPARE NOVEL TETRAOLS

This is a division of application Ser. No. 612,417, filed Sept. 11, 1975 now U.S. Pat. No. 3,991,126.

BACKGROUND OF THE INVENTION

This invention relates to new tetraol compounds which are useful in the preparation of polyether polyols for polyurethanes or as humectants in the tobacco, food and cosmetic industries; and a process for preparing the compounds.

A wide variety of polyhydric alcohols have been reported in the scientific literature. In particular, tetrahydric alcohols, or tetraols, have been reported as useful products for various industrial applications. Pentaerthritol is perhaps the best-known tetraol, and has gained popular acceptance due to its unique symmetrical structure and consequent stability. Pentaerythritol is prepared by the reaction of an aqueous acetaldehyde solution with excess paraformaldehyde in the presence of calcium hydroxide. The widespread industrial use of this tetraol has kindled interest in developing alternative tetraols. For example, U.S. Pat. No. 2,839,472, granted Oct. 1, 1974, describes an improved process for preparing the tetraol 2,2,5,5-tetramethyl-1,3,4,6-hexatetraol. The process calls for the reaction of hexahydro-3,3,6,6-tetramethylfuro[3,2-b]furan-2,5-diol with hydrogen in the presence of water and a nickel catalyst.

SUMMARY OF THE INVENTION

It has now been found that novel tetraols, as hereinafter described, can be prepared from a readily available mixture of unsaturated diols by a selective epoxidation and hydroxylation process.

DETAILED DESCRIPTION OF THE INVENTION

The novel tetraols of this invention are viscous, water-soluble liquids which are stable up to about 200° C under neutral or basic conditions, but undergo decomposition in the presence of acids. The tetraols have the general structure

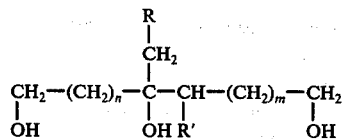

wherein R and R' are either hydrogen or hydroxy and differ from one another, n is an integer from 1 to 6, and m is an integer from 0 to 6. In accordance with the above structure, tetraols contemplated by this invention include those compounds wherein R is hydroxy and R' is hydrogen such as:

3-hydroxymethyl-1,3,5-pentanetriol;
3-hydroxymethyl-1,3,6-hexanetriol;
3-hydroxymethyl-1,3,8-octanetriol;
3-hydroxymethyl-1,3,10-decanetriol;
4-hydroxymethyl-1,4,6-hexanetriol;
5-hydroxymethyl-1,5,8-octanetriol;
6-hydroxymethyl-1,6,10-decanetriol; and
7-hydrpxymethyl-1,7,14-tetradecanetriol.

The above structure also contemplates tetraols wherein R is hydrogen and R' is hydroxy, such as:

3-methyl-1,2,3,5-pentanetetraol;
4-methyl-1,3,4,6-hexanetetraol;
5-methyl-1,4,5,7-heptanetetraol;
8-methyl-1,7,8,11-undecanetetraol;
8-methyl-1,7,8,12-duodecanetetraol; and
8-methyl-1,7,8,14-tetradecanetetraol.

3-hydroxymethyl-1,3,5-pentanetriol and 3-methyl-1,2,3,5-pentanetetraol are particularly suitable for industrial applications and are therefore preferred tetraols.

The tetraols of this invention are readily prepared by epoxidation of unsaturated diols selected from the group consisting of diols of the formulas

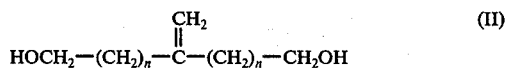

wherein m and n are as previously defined, to form the corresponding 1,2-epoxides; and hydroxylation of the epoxides to form the corresponding tetraols. By starting with diols of formula (II), hereinafter referred to as methylene alkane diols, tetraols of formula (I) wherein R is hydroxy and R' is hydrogen are readily prepared. Similarly, by starting with diols of formula (III), hereinafter referred to as methyl alkene diols, tetraols of formula (I) wherein R is hydrogen and R' is hydroxy are readily prepared.

A thorough description of the epoxidation of unsaturated compounds and the hydroxylation of epoxides can be found in "Chemistry of Organic Compounds," Noller (Ed.), W. B. Saunders Co., 1966, the teachings of which are incorporated herein by reference. In general, the epoxidation of an unsaturated diol with a peroxy acid is exothermic. Accordingly, cooling will be required to maintain a satisfactory temperature within the range from about 5° to about 40° C, preferably from about 10° to about 20° C. The reaction will proceed at atmospheric pressure within a period of a few hours. In most instances, complete epoxidation will take about 3 hours. Peroxy acids (per acids) are acyl hydroperoxides and result from the acid-catalyzed reaction of an acid with hydrogen peroxide. Peroxyacetic acid, a preferred peroxy acid, is made also by the oxidation of acetaldehyde. Peroxy acids readily add oxygen to unsaturated compounds to give the three-membered oxirane ring. Such compounds commonly are called "epoxides" and the process is known as "epoxidation". The reaction is first order in both olefin and peroxy acid. The rate increases with increasing acidity of the peroxy acid and with increasing electron-releasing property of substituents at the double bond. Since the reaction goes faster in nonpolar than in polar solvents, it is assumed that proton transfer takes place intramolecularly. Hydroxylation of the epoxides is achieved by heating to a temperature of at least about 120° C, preferably at least about 145° C, in the presence of water.

The diols useful in the preparation of the novel tetraols of this invention are described in the prior art and can be prepared by a variety of procedures.

Unsaturated diols useful herein are readily prepared by several synthetic methods. The preferred route is by the reaction of two mols of formaldehyde with one mol of a methyl-branched olefin. The reaction is carried out by heating a mixture of an olefin and aqueous formaldehyde in isopropyl alcohol at a pH of 6 to 7 to a temperature in the range of 150° C to 300° C, under pressure for 0.5 to 2 hours. The product is isolated and purified by distillation under reduced pressure. Other processes of this type are described in U.S. Pat. Nos. 2,426,017 and 3,692,848. Another, but similar route, is the reaction of a methyl-branched unsaturated alcohol with formaldehyde. Conditions, work-up, etc. are essentially the same as above, except that only one mol of formaldehyde is employed. See for example, U.S. Pat. No. 2,789,996. Unsaturated alcohol feedstock for this synthesis may be obtained from the reaction of an olefin with one mol of aldehyde, e.g. U.S. Pat. Nos. 2,335,027 and 2,308,192. Unsaturated diols may also be prepared from unsaturated diesters, e.g. diethylcitraconate, by reduction of the ester groups. Usually this reduction is effected by chemical means such as sodium in an alcohol, e.g., ethanol, propanol or butanol. In this procedure, the ester is dissolved in the alcohol, and sodium metal is added at a rate to maintain reflux. The product is isolated and purified by first washing with water and then distilling. Another process for preparing unsaturated alcohols is by the dehydrohalogenation of a haloalkane-alpha, omega-diol. This reaction is effected by heating the diol in an inert solvent in the presence of a molar equivalent amount of a base, e.g. sodium acetate, tertiary amines such as triethylene diamine, etc. The product is recovered by distillation after filtering off the by-product salt. Finally, unsaturated dihalohydrocarbons may by hydrolyzed to give unsaturated diols. This reaction is promoted by base. An amount of base equivalent to two mols of hydrogen halide is used to remove this acid as it is formed. Excess water is used and the reaction temperature is kept low to minimize dehydration.

In many instances, the unsaturated diols useful as starting materials in the preparation of the tetraols of this invention are obtained as mixtures of methylene alkane diols and methyl alkene diols. Accordingly, where it is desirable to prepare tetraols derived from methyl alkene diols, a process which, while employing a mixture of diols, selectively yields only the desired tetraols would be advantageous. It has been found that, when a mixture of diols is epoxidized using less than the stoichiometric amount of a peroxy acid, methyl alkene diols are preferentially epoxidized. Preferential epoxidation will occur independently of the mol ratio of the various diols in the mixture; however, it is preferable that the starting mixture comprise methylenealkane diols and methylalkene diols at a mol ratio of about 1:1.

Thus, in its process embodiment, the present invention provides a process for selectively preparing tetraols of the formula

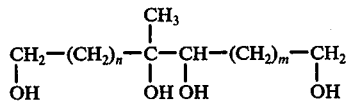

wherein $n$ is an integer from 1 to about 6 and $m$ is an integer from 0 to about 6, from a mixture of unsaturated diols of the formula

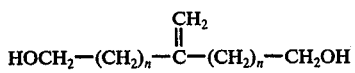

and diols of the formula

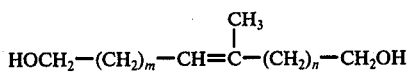

wherein $n$ is an integer from 1 to about 6 and $m$ is an integer from 0 to about 6, comprising the steps of: (1) reacting said diol mixture with less than the stoichiometric amount of a peroxy acid to prepare an epoxide; and (2) hydroxylating the epoxide of the first step to prepare a tetraol. The tetraol can be separated from the reaction product by conventional separatory techniques such as distillation.

EXAMPLES

While the compounds and process of this invention have been described above, the following examples further illustrate the practice of this invention.

EXAMPLE 1

Preparation of 3-methyl-1,2,3,5-pentanetetraol

A one-liter, 3-necked flask equipped with magnetic stirrer, thermometer, condensor and dropping funnel was charged with 46.4 g of a diol mixture comprising 53.5%, by weight, 3-methylene-1,5-pentanediol and 45.0%, by weight, 3-methyl-2-pentene-1,5-diol dissolved in 400 ml of trichloromethane.

A solution of 38.0 g of 40% peracetic acid (0.2 molar in acetic acid) and 3.8 g of 0.2M sodium acetate trihydrate was added to the dropping funnel.

The peracetic acid solution was added dropwise to the diol mixture with constant stirring over a 33-minute period. The reaction mixture was cooled in an ice bath to maintain a temperature from 3° to 8° C.

Following addition, the reaction mixture was stirred for 30 minutes at 0° and then 3 hours at 18° C. The mixture was subsequently neutralized with 376 g of sodium carbonate powder, and 200 ml of trichloromethane was added to facilitate stirring.

Following neutralization, the supernatant liquid had a pH of 7 and no peroxide could be detected by KI starch paper. The reaction mixture was filtered, and the solids were washed with trichloromethane. The trichloromethane was evaporated from the filtrate at room temperature under vacuum.

A 47.7-g portion of the filtrate was dissolved in 477 ml of distilled water and heated in a one-liter autoclave at about 145° C for 130 minutes. The pH decreased from 6.8 to 5.2.

A 196.4-g portion of the hydrolysate was neutralized with 10% sodium hydroxide to a pH of 10.5. Water was removed under vacuum and the residue was vacuum distilled, yielding 3 fractions:

| | |
|---|---|
| (1) 95° C–135° C/0.3–0.4 mm Hg | 7.6 g |
| (2) 135° C–170° C/0.3–0.4 mm Hg | 1.1 g |
| (3) 170° C–180° C/0.3–0.4 mm Hg | 6.2 g |

Fraction (1) was found to be 3-methylene-1,5-pentanediol. Fraction (3) was found to be 3-methyl-1,2,3,5-pentanetetraol. The intermediate fraction (2) was found to be a mixture of 3-methylene-1,5-pentanediol and 3-methyl-1,2,3,5-pentanetetraol.

EXAMPLE 2

Preparation of 3-hydroxymethyl-1,3,5-pentanetriol

Using the procedure of Example 1, an 11.6-g portion of 3-methylene-1,5-pentanediol dissolved in 100 ml of trichloromethane was epoxidized using 19.0 g of 40% peracetic acid and 1.9 g of $NaOCOCH_3$.

A 12.0-g portion of the epoxide was dissolved in 250 ml of distilled water and heated at about 145° C for 2 hours. The resulting hydrolysate was neutralized with 10% sodium hydroxide to a pH of 10.5 and vacuum distilled at 185° to 187° C/0.4 mm, yielding 4.75 g of 3-hydroxymethyl-1,3,5-pentanetriol.

What is claimed is:

1. A process for preparing tetraols of the formula

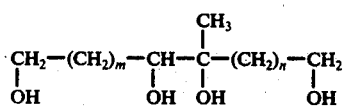

wherein $n$ is an integer from 1 to about 6 and $m$ is an integer from 0 to 6, from a mixture of unsaturated diols comprising methylene alkane diols of the formula

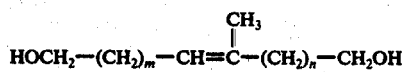

and methyl alkene diols of the formula $$HOCH_2-(CH_2)_m-CH=\overset{CH_3}{\underset{|}{C}}-(CH_2)_n-CH_2OH$$

wherein $n$ and $m$ are as defined above, which comprises the steps of: (1) contacting said mixture of unsaturated diols with less than the stoichiometric amount of a peroxy acid to selectively epoxidize the methyl alkene diols of said mixture; and hydroxylating the epoxide of the first step in the presence of water at a temperature of at least about 120° C.

2. A process according to claim 1 wherein said diol mixture comprises methyl alkene diols and methylene alkane diols at a mol ratio of about 1:1.

3. A process according to claim 2 wherein said diol mixture comprises 3-methylene-1,5-pentanediol and 3-methyl-2-pentene-1,5-diol.

* * * * *